United States Patent
Repins et al.

(10) Patent No.: US 9,075,012 B2
(45) Date of Patent: Jul. 7, 2015

(54) PHOTOLUMINESCENCE-BASED QUALITY CONTROL FOR THIN FILM ABSORBER LAYERS OF PHOTOVOLTAIC DEVICES

(71) Applicant: ALLIANCE FOR SUSTAINABLE ENERGY, LLC, Golden, CO (US)

(72) Inventors: Ingrid L. Repins, Morrison, CO (US); Darius Kuciauskas, Lakewood, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 50 days.

(21) Appl. No.: 13/673,581

(22) Filed: Nov. 9, 2012

(65) Prior Publication Data

US 2013/0122612 A1     May 16, 2013

Related U.S. Application Data

(60) Provisional application No. 61/558,315, filed on Nov. 10, 2011.

(51) Int. Cl.
| | |
|---|---|
| G01N 21/64 | (2006.01) |
| G01R 31/26 | (2014.01) |
| G01R 31/265 | (2006.01) |
| H02S 50/10 | (2014.01) |

(52) U.S. Cl.
CPC ........ *G01N 21/6408* (2013.01); *G01R 31/2601* (2013.01); *G01R 31/2656* (2013.01); *G01N 21/6489* (2013.01); *H02S 50/10* (2014.12)

(58) Field of Classification Search
None
See application file for complete search history.

(56) References Cited

U.S. PATENT DOCUMENTS

| | | | | |
|---|---|---|---|---|
| 5,729,012 | A * | 3/1998 | Wood et al. | 250/227.15 |
| 7,968,353 | B2 | 6/2011 | Britt et al. | |
| 8,239,165 | B1 * | 8/2012 | Young et al. | 702/182 |
| 2003/0117628 | A1 * | 6/2003 | Harju et al. | 356/417 |
| 2009/0258444 | A1 * | 10/2009 | Britt et al. | 438/5 |

(Continued)

OTHER PUBLICATIONS

C. Richard Brundle, Charles A. Evans, Jr., Shawn Wilson, and Lee E. Fitzpartrick, Encyclopedia of Materials Characterization, Surface, Interfaces, Thin films,1992, Reed Publishing (USA) Inc., pp. 371-384.*

(Continued)

*Primary Examiner* — Charles Garber
*Assistant Examiner* — Stanetta Isaac
(74) *Attorney, Agent, or Firm* — John C. Stolpa; Suzanne C. Walts; Michael A. McIntyre

(57) ABSTRACT

A time-resolved photoluminescence-based system providing quality control during manufacture of thin film absorber layers for photovoltaic devices. The system includes a laser generating excitation beams and an optical fiber with an end used both for directing each excitation beam onto a thin film absorber layer and for collecting photoluminescence from the absorber layer. The system includes a processor determining a quality control parameter such as minority carrier lifetime of the thin film absorber layer based on the collected photoluminescence. In some implementations, the laser is a low power, pulsed diode laser having photon energy at least great enough to excite electron hole pairs in the thin film absorber layer. The scattered light may be filterable from the collected photoluminescence, and the system may include a dichroic beam splitter and a filter that transmit the photoluminescence and remove scattered laser light prior to delivery to a photodetector and a digital oscilloscope.

23 Claims, 7 Drawing Sheets

(56) References Cited

U.S. PATENT DOCUMENTS

| | | | |
|---|---|---|---|
| 2010/0006785 A1* | 1/2010 | Finarov | 250/559.05 |
| 2010/0087016 A1 | 4/2010 | Britt et al. | |
| 2011/0033957 A1* | 2/2011 | Holden et al. | 438/16 |
| 2011/0117681 A1 | 5/2011 | Bardos et al. | |
| 2011/0177622 A1 | 7/2011 | Britt et al. | |
| 2012/0120387 A1* | 5/2012 | Meloni et al. | 356/72 |
| 2012/0326054 A1* | 12/2012 | Meloni | 250/459.1 |

OTHER PUBLICATIONS

Levi, D., "w-Si characterization: Imaging of diffusion length" PowerPoint IEEE PV, Fort Collins, CO (2009).

Metzger, W.K. et al., "Long lifetimes in high-efficiency Cu(In,Ga)Se2 solar cells," Applied Physics Letters 93, 0221100 (2008).

Repins, I.L. et al., "Measured minority-carrier lifetime and CIGS device performance," IEEE Photovoltaics Specialists Conf. 34 (2009).

Metzger, W.K. et al., "Time-resolved photoluminescence and photovoltaics," 2004 DOE Solar Energy Technologies Program Review Meeting, Oct. 25-28, 2004, Denver, CO, NREL/CP-520-37028.

Metzger, W.K. et al., "Recombination kinetics and stability in polycrystalline Cu(In,Ga)Se2 solar cells," Thin Solid Films 517 (2009) 2360-2364.

Keyes, B.M. et al., "Changes in the dominant recombination mechanisms of polycrystalline Cu(In,Ga)Se2 occurring during growth," Journal of Applied Physics, V 94, No. 9, Nov. 1, 2003.

Ohnesorge, B. et al., "Minority-carrier lifetime and efficiency of Cu(In,Ga)Se2 solar cells," Applied Physics Letters, V 73, No. 9, Aug. 31, 1998.

Weigand, R. et al., "Correlation between minority carrier lifetime and efficiency in CuInSe2 solar cells," 2nd World Conf. and Exhibition on Photovoltaic Solar Energy Conversion, Jul. 6-10, 1998, Vienna, Austria.

Probst, V. et al., "Rapid CIS-process for high efficiency PV-modules: development towards large area processing," Thin Solid Films 387 (2001) 262-267.

Ferenczi, T.A. et al., "On the nature of the fluorenone-based emission in oxidized poly (dialkyl-fluorene)s," Journal of Physics: Condensed Matter (2008).

Geohegan, D.B. et al., "Photoluminescence from gas-suspended SiOx nanoparticles synthesized by laser ablation," Applied Physics Letters, vol. 73, No. 4, Jul. 27, 1998.

Shirakata, S. et al., "Photoluminescence and time-resolved photoluminescence in Cu(In,Ga)Se2 thin films and solar cells," Phys. Status Solidi C 6, No. 5, 1059-1062 (2009).

Scheer, R. et al., "Advanced diagnostic and control methods of processes and layers in CIGS solar cells and modules," Progress in Photovoltaics: Research and Applications, 2010; 18: 467-480.

Sakurai, T. et al., "Time-resolved microphotoluminescence study of Cu(In,Ga)Se2," Japanese Journal of Applied Physics 50 (2011).

"CIS carrier lifetime measurement system" http://www.nanoplus.com/content/view/58/90/, Nanoplus product information, accessed Nov. 6, 2012.

Laytec in-situ sensors "Pearl" http://www.laytec.de/182.html, product information, accessed Oct. 31, 2012.

* cited by examiner

PHOTOLUMINESCENCE-BASED QUALITY CONTROL FOR THIN FILM ABSORBER LAYERS OF PHOTOVOLTAIC DEVICES

CROSS-REFERENCE TO RELATED APPLICATIONS

This application claims the benefit of U.S. Provisional Application No. 61/558,315 filed Nov. 10, 2011, which is incorporated herein by reference in its entirety.

CONTRACTUAL ORIGIN

The United States Government has rights in this invention under Contract No. DE-AC36-08GO28308 between the United States Department of Energy and the Alliance for Sustainable Energy, LLC, the Manager and Operator of the National Renewable Energy Laboratory.

BACKGROUND

Thin film devices may be used to create solar cells, detectors, electronic devices, telecommunication devices, charge-coupled imaging devices (CCDs), computers, and even biological or medical devices (together considered "thin-film compound semiconducting materials"). With regard to renewable energy, solar cells are photovoltaic (PV) devices that have characteristics that enable them to convert the energy of sunlight into electric energy. The aim of research often is to achieve solar cell designs with the lowest cost per watt generated by the solar cell, and, concurrently, the designs should provide solar cells that are suitable for inexpensive commercial production. With regard to this latter concern, it is often difficult to provide adequate quality control for the various layers of the thin film PV device as it is being fabricated or in "real time."

For example, when manufacturing a semiconductor or thin film PV device in which the light-absorbing layer is composed of copper, indium, gallium and selenium (a CIGS device), the CIGS layer (or thin film absorber layer) is the most difficult in the device stack to form and control. Similar issues over quality control exist for fabricating other thin film absorber layers, e.g., a thin film of cadmium telluride (CdTe) for a CdTe device. In the case of a CIGS device, control is difficult compared to other semiconductors because there are four constituent elements to control and fabrication may be complicated by sodium doping, high temperatures, and grading through the thin film. Unfortunately and undesirably, the quality of the CIGS layer is typically not known until after the entire device is manufactured with quality control tests performed electrically with contacts connected to upper and lower conductor layers. This situation precludes real time evaluation and optimization of the CIGS layer.

$Cu(In, Ga)Se_2$ (CIGS) solar cells have achieved efficiencies in excess of 20 percent. CIGS devices are also able to be manufactured with various different manufacturing processes and techniques. Accordingly, CIGS is a leading candidate to displace silicon in the photovoltaics market. Nevertheless, there is still a challenge to characterize fundamental CIGS properties, such as carrier concentration and recombination in absorber layers. Further, without real time feedback on specific electro-optical properties, it is difficult to distinguish good from bad material in deposited thin films, to understand performance variations, to optimize growth processes, and to control this complex quaternary material. As noted above, it is desirable to provide similar real time quality control during the forming or deposition of other thin film absorber layers rather than having to wait to perform such testing on the finished PV device via electrical techniques.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

It was recognized by the inventors that it would be highly desirable to measure the quality of a thin film absorber layer, such as film of CIGS, as soon as the layer is deposited so that the measured or determined quality (one or more quality control parameters) may be provided as feedback in the fabrication process. With this in mind, it was understood that photoluminescence-based methods may provide a way to provide such real time measurement of the quality of a thin film absorber layer. Such a real time quality control method (and systems that implement such a method) allows manufacturers of PV devices to perform real time evaluation and optimization of the thin film absorber layer (e.g., a film of CIGS or the like).

Photoluminescence is a process in which a substance absorbs photons or electromagnetic radiation and then re-radiates photons. Quantum mechanically, this may be illustrated as an excitation to a higher energy state and then a return to a lower energy state accompanied by the emission of a photon. This is one of many forms of luminescence or light emission and is distinguished by photo excitation or excitation by photons. Because the time period between absorption and emission is generally extremely short, e.g., in the order of about 10 nanoseconds, the inventors determined that photoluminescence would be well-suited for use in a thin film quality control method and system to provide near immediate measurements of the optical properties of the material of a thin film.

In particular, it was recognized by the inventors that several useful embodiments of photoluminescence-based quality control systems and methods may be provided using time-resolved photoluminescence (TRPL) where a sample is excited with a light pulse and then the decay in photoluminescence with respect to time is measured. As will be described in greater detail below, this technique is useful in measuring the minority carrier lifetime of semiconductor material and, therefore, useful in the quality control systems and methods described herein (e.g., for performing quality control measurements on a CIGS absorber layer or other thin film absorber layer). For example, this minority carrier lifetime ("lifetime", as used herein) may be determined for a thin film absorber layer and provided as a quality control measurement or parameter (or feedback) for use in modifying operation of thin film deposition/fabrication equipment and/or to select thin films for use in complete PV devices (e.g., remove partially formed PV devices from a production line when the lifetime is outside of a predefined acceptable band or range).

Briefly, a quality control system is described for measuring TRPL from a thin film absorber layer and correlating TRPL data to absorber quality, via extraction of minority carrier lifetime (or simply "lifetime") and relative carrier density. The following aspects of the system make it useful and suitable for in situ characterization of CIGS and other thin film absorbers. First, embodiments of the system may use an optical fiber to deliver the exciting beam (or collimated light) from a pulsed light source (e.g., a laser) and to collect the emitted light from the sample (e.g., a deposited thin film absorber layer). Use of a single optical fiber is achieved in some cases by providing a dichroic beam splitter in the light path between the laser and the sample that acts to direct the collected light toward a photodetector. Further, a longpass or bandpass filter may be provided between the beam splitter and the photodetector, with the filter selected to transmit only photoluminescence (PL) and block scattered light.

Second, some embodiments of the system may use a high speed digitizing device, such as a digital oscilloscope, to process output of the photodetector. Use of a digital oscilloscope allows up to 1 million measurements or more per second. Further, many measurements can be averaged to reduce the signal-to-noise ratio. Third, the system may include a low-power, pulsed diode laser for the collimated light source. Fourth, the quality control system may implement the photodetector portion or component using a solid state photodetector such as a photomultiplier or a photodiode.

Fifth, the optics of the system may be adapted to collect a broad spectrum (e.g., 1000 to 1300 nanometers (nm)) of light from the sample. A broad band system is an improvement from devices operating at a single wavelength (e.g., a detector with a 10 nm bandwidth or similar narrow band). Use of broad band collection is useful for thin film absorber layers, such as CIGS films, that have a variable band gap (e.g., CIGS has a variable band gap related to the Ga content) and low fluorescence intensity, to more accurately determine lifetime. Further, collecting a broad spectrum maximizes (or significantly increases) the amount of collected fluoresced light reaching the photodetector, which desirably modifies (e.g., lowers/lessens certain) requirements for the detector and the laser. Sixth, the system may also use polarization-insensitive optics to increase the amount of fluoresced light collected by the photodetector. As will be appreciated, several of these features of the system facilitate the use a low-powered, pulsed diode laser (lower intensity light source) for sampling the thin film with low incident intensity.

More particularly, a photoluminescence-based system is provided for use in facilitating quality control during manufacture of thin film absorber layers for photovoltaic devices. The system includes a collimated light source generating an exciting beam, and the system also includes an optical fiber with an end both directing the exciting beam onto a thin film absorber layer and collecting TRPL signal from the thin film absorber layer. Use of a single fiber makes the instrument suitable for in-situ or in-line use and allows easy sample positioning with relatively high tolerance. The end of the fiber may be positioned up to about 1 cm away from the absorber layer surface (e.g., micrometers up to 1 cm). Further, the system includes a processor (e.g., software, firmware, and/or hardware as may be provided on a computing device) that functions to determine a quality control parameter of the thin film absorber layer based on the collected TRPL signal.

In some cases, the processor generates a feedback signal controlling fabrication equipment operable to manufacture a PV device including the thin film absorber layer such as to modify deposition parameters to improve minority carrier lifetime. In some implementations of the system, the collimated light source comprises a low power, pulse diode laser having photon energy at least great enough to excite electron hole pairs in the thin film absorber layer. In this regard, the scattered laser light may be filtered from the collected TRPL signal and, then, the system may include a filter (such as a long pass filter or a bandpass filter) prior to the collected light reaching a photodetector.

In some embodiments, the thin film absorber layer comprises a thin film of CIGS, CdTe, or CZTS. The photodetector may be adapted for detecting a broad spectrum (e.g., a range of band widths in the range of 800 to 1300 nm) and for receiving the collected fluoresced light and, in response, generating a detector signal. For example, the photodetector may be a photodiode or a thermo-electrically cooled photomultiplier tube. The system may include a digital oscilloscope that processes the detector signal and provides its output to the processor for use in determining the quality control parameter (e.g., a minority carrier lifetime).

According to another aspect, a method is provided for monitoring fabrication of a thin film absorber. The method includes providing a sample with an exposed absorber layer, and then detecting emitted light from the absorber layer over a range of at least 50 nm within a range of 800 to 1300 nm. The method also includes correlating the detected emitted light or PL signal to a quality control parameter for the absorber layer (e.g., lifetime for a film of CIGS, CdTe, CZTS, or the like).

In some embodiments, the detecting is performed with an assembly comprising a photodiode or a photomultiplier tube and further including a digital oscilloscope. The method may also include operating a laser to provide an exciting beam to the absorber layer prior to the detecting, wherein the exciting beam is separable from the detected emitted light or PL signal (e.g., the laser is a low power, pulsed-diode laser providing beams in the range of 600 to 800 nm). Some implementations of the method may include, with a single fiber, directing the exciting beam onto the absorber layer and collecting the emitted light from the absorber layer for use in the detecting step.

In addition to the exemplary aspects and embodiments described above, further aspects and embodiments will become apparent by reference to the drawings and by study of the following descriptions.

BRIEF DESCRIPTION OF THE DETAILED DRAWINGS

Exemplary embodiments are illustrated in referenced figures of the drawings. It is intended that the embodiments and figures disclosed herein are to be considered illustrative rather than limiting.

DESCRIPTION

The following description is directed generally to systems and methods for providing in situ and real time quality control during fabrication of thin-film photovoltaic (PV) devices that include a thin film absorber layer (e.g., a thin film of CIGS or the like). To this end, quality control systems and methods are presented that utilize time-resolved photoluminescence (TRPL) to determine lifetime of a deposited thin film prior to further fabrication of a PV device, and the determined lifetime may be used as feedback to the deposition equipment to allow deposition or other operating parameters to be adjusted on-the-fly or, at least, more promptly.

CIGS materials are commonly used in solar cells and other semiconductor devices. Accordingly, in one or more embodiments described below, a short laser pulse injects excess electrons and holes into the CIGS layer (or other thin film absorber layer), and the resulting luminescence is tracked as a function of time. The photoluminescence (PL) intensity is proportional to the product of electron and hole concentrations. So, in low-injection conditions, where the excess carrier concentration $\Delta n$ is much less than the equilibrium majority-carrier concentration $p_0$, the PL intensity is proportional to $p_0 \Delta n$. In high-injection conditions, $\Delta n$ is much greater than $p_0$, and the PL signal is proportional to $\Delta n^2$. In either case, though, the excess carrier concentration may be tracked by monitoring the PL signal, even when the dominant recombination mechanism is nonradiative. Under conditions of low injection (i.e., low intensity excitation), the time decay of the monitored PL signal can be used to determine minority carrier lifetime with the initial PL intensity being proportional to majority carrier density. These quantities can be used to determine the quality of the thin film.

Figure 1:
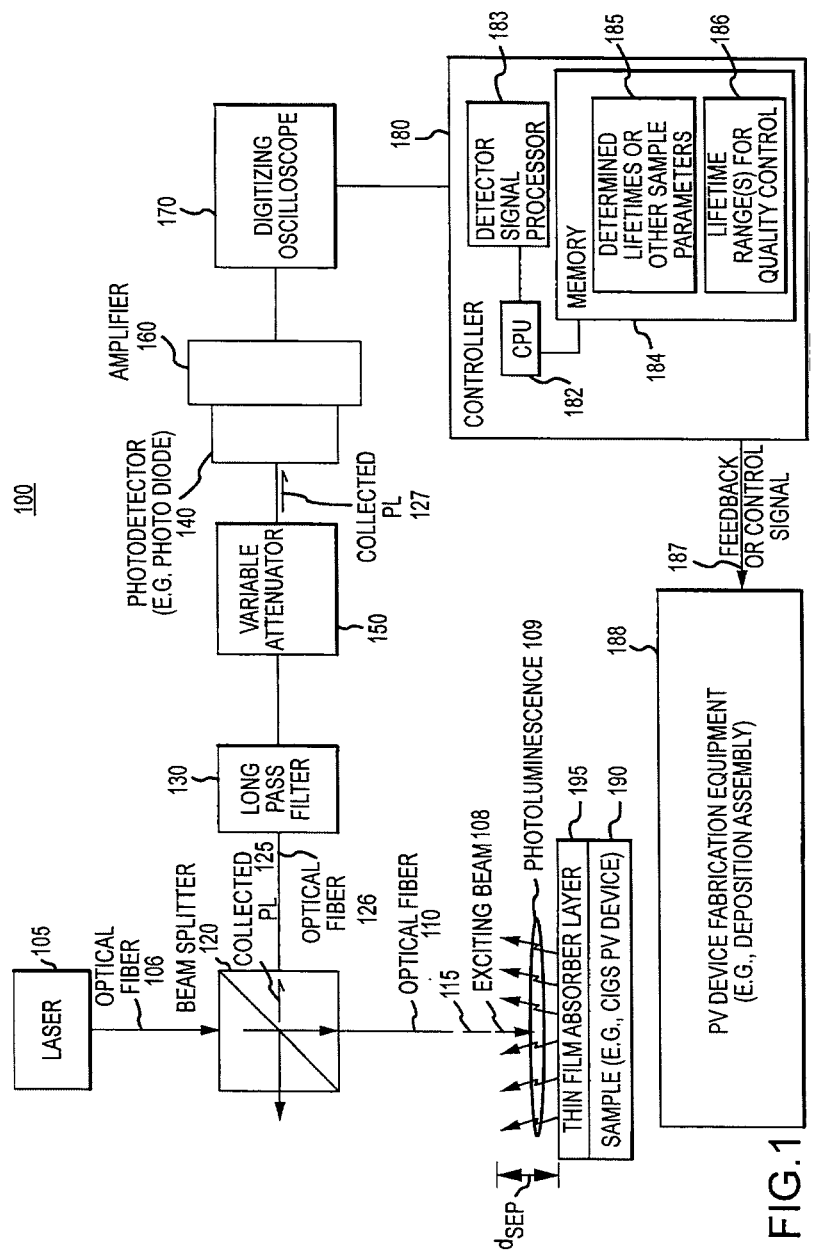
FIG. 1 shows a block diagram of fiber-fed, time-resolved, photoluminescence quality control system according to a first embodiment.

FIG. 1 shows a block diagram of an in-situ, fiber-fed, time-resolved, photoluminescence-based quality control system 100. In the system 100 of FIG. 1, an exciting beam 108 is delivered using the same optical fiber 110 with which the emitted light or PL signal 109 from the sample 190 is collected. The exciting beam 108 is provided by a collimated light source 105 such as, but not limited to, low-power pulsed laser. The optical path for the exciting beam 108 is shown to include an optical fiber 106 that directs the collimated light output of the laser 105 to a dichroic beam splitter 120, which directs laser light along the path to the sample, as shown.

The laser light output from the beam splitter 120 is directed onto the optical fiber 110 and is output from a fiber end 115 as the exciting beam 108. The exciting beam 108 strikes a thin film absorber layer 195 on the sample (e.g., a partially fabricated PV device or the like) 190, and, in response, PL 109 is generated by the material of the layer 195. This material may be CIGS, CdTe, a kesterite such as CZTS or the like, or any other material used to provide thin film absorber layers for PV devices. The optical fiber 110 via end 115 also collects the PL 109 and other light (e.g., reflected laser light), and this collected light 125 is separated by the dichroic beam splitter 120. Only the PL light 109 is redirected by the beam splitter 120 and is directed into another optical fiber 126, which provides a light path to a photodetector 140.

In this way, the optical fiber 110 acts as a single fiber for both delivering the exciting beam 108 to the absorber layer 195 and also for collecting the PL 109 from the surface of the sample 190. In other words, the laser 105 provides a beam of light 108 with one color while the PL 109 is a second and different color that can be collected and processed to determine optical properties of the thin film absorber layer 195.

Use of a single fiber 110 simplifies the implementation in-situ and permits collection of a greater fraction of the photoluminescence when the fiber 110 is positioned in close proximity to the CIGS sample 190. In this regard, the separation distance, $d_{sep}$, between the fiber end (outlet) 115 and the layer 195 may be several micrometers to 2 centimeters, with some embodiments successfully using a separation distance, $d_{sep}$, of about 1 centimeter to collect adequate amounts of collected light 125 while also providing a desirably sufficient clearance between end 115 and layer 195. Avoiding contact may be important, for example, in a production facility where sample 190 is part of a rapidly moving fabrication line as typical in a PV device manufacturing facility.

The use of a single optical fiber (with fiber 106 and 110 sometimes being considered part of a single fiber) is made possible, in part, by use of a dichroic beam splitter 120. The dichroic beam splitter 120 is configured or selected so as to allow an exciting beam 108 from laser 105 to pass into fiber 110 and onto layer 195 while also acting to redirect all or a large portion of the collected light 125 into optical fiber 126 and onto a path to photodetector 140.

The system 100 further is shown to include one or more pre-detector components that function to preprocess or precondition the collected light 125 prior to delivery to the photodetector 140. The dichroic beam splitter 120 may be considered a first component of this preconditioning assembly as it acts to direct all or most of the collected PL in collected light 125 toward the photodetector 140 and also prevents most of the collected laser light from reaching the detector 140. A second component of the preconditioning assembly may be a filter 130 that acts to further clean up the collected light to contain only or mostly the PL light as shown at 127. For example, the filter 130 may be a long pass or band pass filter to remove exciting laser light before the detector 140. Another preconditioning assembly component may be a variable attenuator 150 utilized to control optical power levels to protect the photodetector 140 from damage.

Figure 2:
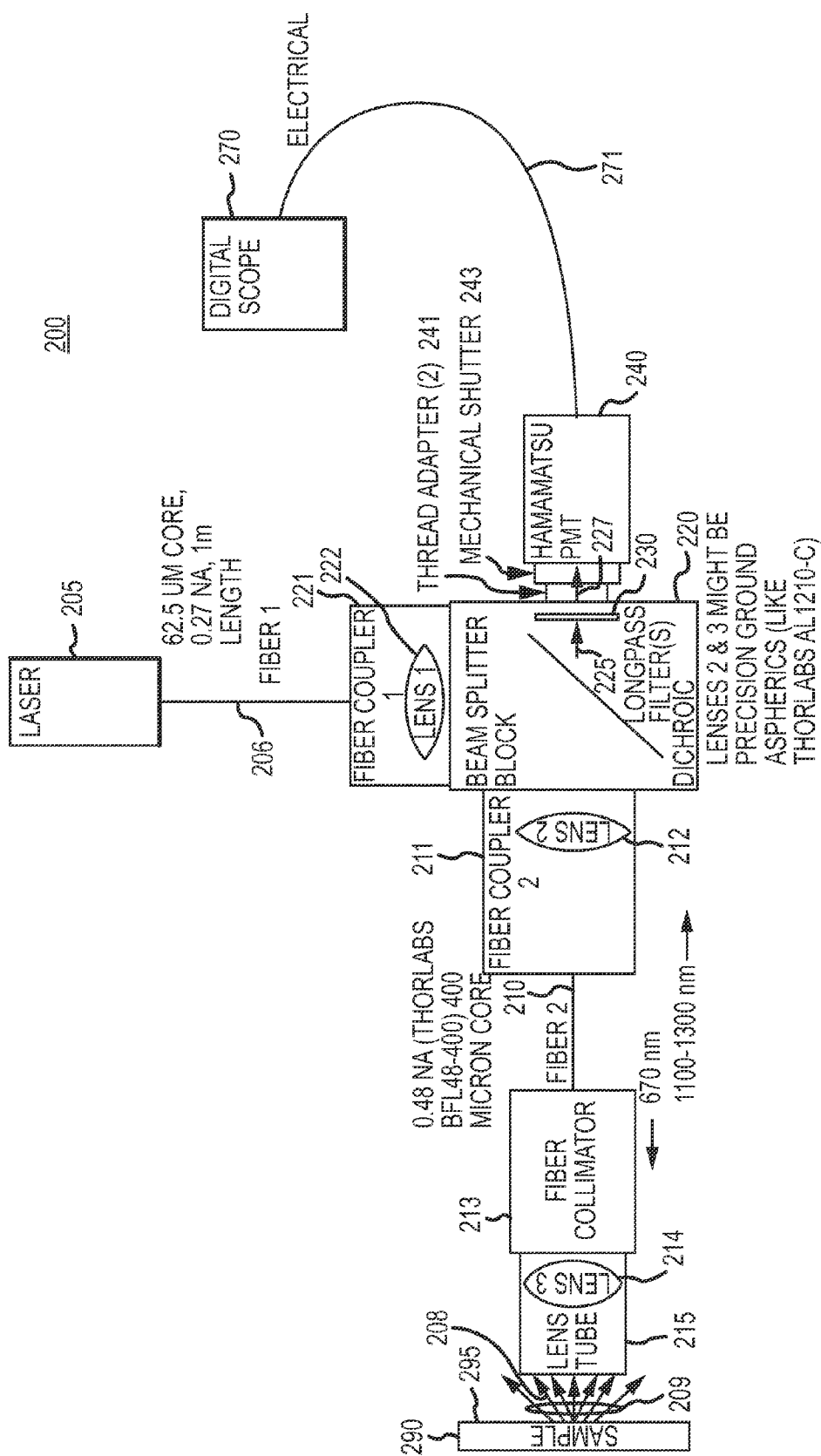
FIG. 2 shows a block diagram of fiber-fed time-resolved photoluminescence quality control system according to a second embodiment.

The detector 140 is positioned in the system 100 to receive the collected PL light 127 and output an electrical signal that is a function of received light intensity. This component may generally be considered a PL detector or photodetector. The photodetector 140 may, for example, take the form of a photodiode, a photomultiplier (PMT), or other photodetector. An amplifier 160 may also be used to amplify the output signal from the photodetector 140 (e.g., a photodiode) before the signal is received by (provided to) a digitizing component 170 for further processing and/or data collection/accumulation. In some cases, use of a photodiode may be useful as this allows one to avoid use of liquid nitrogen cooling, which may be beneficial in a manufacturing setting. In other cases (as shown in FIG. 2), a thermo-electrically cooled PMT may be utilized for photodetector 140. In yet other embodiments, the use of liquid nitrogen or similar coolants may be employed to cool photodetector 140 when appropriate.

Digitizing component 170 may include a digitizing oscilloscope or other high speed device that generates digital signals from the electrical output of photodetector 140. The digitizing component 170 may be connected to a controller 180 for further processing of the signal and digitized output. The controller 180 (e.g., a computer or similar processing device) is shown to include one or more processors 182 that manage operations of (or run) a detector signal processor 183 and memory 184. The signal processor 183 functions to process output of the digitizing oscilloscope 170 to determine or predict properties or parameters of the absorber layer 195 based on the collected PL 127 received at the photodetector 140. For example, minority carrier lifetime can be extracted from the PL signal 127. The signal processor 183 may be implemented using software (computer code), firmware, hardware, or a combination thereof.

Minority carrier lifetime could be determined by the signal processor 183 by fitting a time-dependent PL signal to the mathematical function. In one embodiment, a quality metric, referred to herein as a "figure of merit," is calculated by controller 180 as a function of both the intensity of PL signal 127 received by the photodetector 140 and associated minority carrier lifetime. In one embodiment, figure of merit is calculated based on a formula equivalent to: Figure of Merit=Constant*ln(minority carrier lifetime*√(intensity)). The quantities are combined in this fashion since under low-injection conditions initial luminescence intensity should be proportional to the majority carrier density.

The signal processor 183 or another controller component may then further function to store the determined Figures of Merit, minority carrier lifetimes, and/or intensity (or other sample parameters/characteristics) 185 in memory 184 (at least temporarily). These determined parameters 185 may be provided as output such as in a graph in a user interface of the controller 182 or a linked device (not shown). In other cases, the controller 180 may act to compare the determined lifetimes 185 with a previously defined and stored set of lifetime ranges 186 to be used in quality control during manufacture of a run of PV devices.

For example, a feedback or control signal 187 may be generated by the controller 180 based on processing of the collected fluoresced light 127, and this signal 187 may be transmitted in a wired or wireless manner to PV device fabrication equipment 188 to control operations. In one case, oscilloscope output based on the PL signal 127 may be processed by the signal processor 183 to determine lifetimes 185 or Figures of Merit, and these parameters 185 may be outside of or nearly outside of an acceptable range 186 for PV devices (e.g., CIGS, CZTS, or other materials). In response, a real time control signal 187 may be provided to PV device fabrication equipment 188 to cause modification of one or more fabrication parameter (e.g., to change a parameter being used in the deposition of the film 195) or to cause a sample 190 to be removed from an assembly line as being unacceptable for use in a PV device (e.g., to identify pass/fail samples 190 for use in PV devices). In this manner, the system 100 is useful for providing real time feedback regarding the quality of an absorber layer 195 using optical techniques rather than having to wait hours for post-PV device production testing using electrical techniques. The system 100 is also useful for identifying which step of the module fabrication is off-optimum when electrical techniques indicate poor performance of the entire module.

Operation of the system 100 provides a new method for predicting the performance of Cu(In, Ga)Se$_2$ (CIGS) and other PV devices with thin film absorbers when only the absorber layer has been deposited during manufacturing. This is suitable for in-situ (i.e., within the deposition chamber) use and, thus, shortens by orders of magnitude the time between when the CIGS (or other absorber layer) is deposited and when it can be evaluated. This method permits the measurement of the quality of the CIGS layer as soon as the layer is deposited. Heretofore, after the deposition of the CIGS layer, one had to wait hours in a manufacturing facility or days in a research laboratory for the information regarding the quality of the CIGS layer to be generated. The present method may shorten this quality loop time by nearly a factor of 1000. The correlation between lifetime, as measured by time-resolved photoluminescence (TRPL) and as implemented in system 100, has been established, and the embodiment of system 100 expands and modifies TRPL analysis to permit in-situ TRPL use in CIGS and other absorber layer deposition/fabrication. The system 100 may be implemented so as to be compact and inexpensive as well as requiring only low amounts of maintenance.

The embodiment presented in FIG. 1 utilizes a single fiber 110 to both deliver the exciting beam 108 and to collect the PL signal 109. This is achieved, in part, via a dichroic beam splitter 120 and a long pass filter 130 in the particular embodiment shown in FIG. 1. The system 100 permits easy implementation of TRPL measurement within a vacuum deposition chamber (not shown but may be part of equipment 188), simplifies positioning of the fiber 110 in close proximity to the CIGS sample 190, and maximizes light collection by using a single fiber placed in proximity to sample 190 (e.g., single fiber to provide outlet for beam 108 and inlet for collection of fluoresced light 109 such that the outlet and inlet or co-located). This TRPL-based quality control system 100 also utilizes a digitizing component 170 (such as a digital oscilloscope), which permits approximately 1 million measurements per second. Moreover, many measurements may be averaged in order to reduce signal to noise ratio.

In the system 100, the collimated light source 105 may be a low-power, pulsed diode laser, rather than an expensive and potentially unsafe higher power laser. The use of such a lower intensity laser is acceptable due to the use of the pre-conditioning components such as filter 130 and use of the photodetector 140 and digitizing oscilloscope 170, which act to collect a broad spectrum of PL 127. This TRPL system 100 may also use a solid state photodetector 140, which does not require liquid nitrogen cooling. Liquid nitrogen cooling may be a rather high maintenance and unsafe implementation in a manufacturing environment.

In one embodiment, the TRPL-based system 100 utilizes optics that collect a broad spectrum, for example for CIGS materials in the range of 1000 to 1300 nm, of light 127. A broad spectrum collector is valuable for CIGS sample measurements (and other absorber measurement), as CIGS has a variable band gap related to the Ga content, and use of a broad spectrum collector may maximize the amount of light reaching the detector 140, minimizing the requirements on the detector and laser. The system 100 may also utilize polarization-insensitive optics to collect as much fluoresced light as possible. The TRPL-based system 100 may further utilize a fiber-end collimator and focusing lens (not shown in FIG. 1) to maximize signal collection, while permitting centimeters of separation, $d_{sep}$, between the sample 190 and the fiber end 115.

FIG. 2 shows a block diagram for another embodiment of a fiber-fed, time-resolved, photoluminescence quality control system 200 (which may be a particular implementation of system 100). The system 200 includes a low power, pulse diode laser 205 that is linked to a dichroic beam splitter 220 via optical fiber 206 (e.g., a 62.6 μm core diameter, 0.27 NA, 1 m length graded index multimode optical fiber) and fiber coupler 221 with a first lens 222 (as a non-limiting example of one useful collimated light source 105 for system 100). The laser 205 is operated to provide an excitation beam that is passed from the dichroic beam splitter 220 to an optical fiber 210 via a fiber coupler 211 with a lens 212. The optical fiber 210 includes a fiber collimator 213 and a lens tube with lens 214 defining a fiber outlet/end 215.

During operation of the system 200, the laser 205 provides an excitation beam 208 that is directed out from lens tube/outlet lens 214 and fiber end 215 onto an absorber layer 295 of a sample 290 (e.g., a partially fabricated PV device with the thin film of absorber material). The excitation beam 208 may be provided at an appropriate wavelength with the illustrated system 200 operating the laser 205 to provide a 670 nm beam 208 to sample 290.

The optical fiber 210 is used to deliver the excitation beam 208 and also collect light from sample including a portion of the fluoresced light 209, and the dichroic beam splitter 220 acts to direct this collected light 225 (e.g., at a broad spectrum from 800 to 1300 nm with 1100 to 1300 nm shown in FIG. 2 while other embodiments may capture the 800 to 1100 nm spectrum) to a photodetector 240. Between the photodetector 240 and the beam splitter 220 may be provided one or more filters 230 or other pre-detector conditioning components (functioning as described above in system 100) as well as connectors/components such as thread adapters 241 and a shutter 243.

The photodetector 240 is linked via electrical connecting cable 271 to a digital oscilloscope 270 such that the output signals from the PMT or other photodetector are provided to the oscilloscope 270 for accumulation and/or processing. The oscilloscope 270 typically would provide output to a computer or other controller for use of the oscilloscope output to determine sample characteristics such as lifetime based on the PL signal 209, and, in response, to provide the output to personnel monitoring PV device manufacture and/or to provide real time feedback to fabrication equipment (as discussed above with regard to system 100 of FIG. 1).

Figure 3:
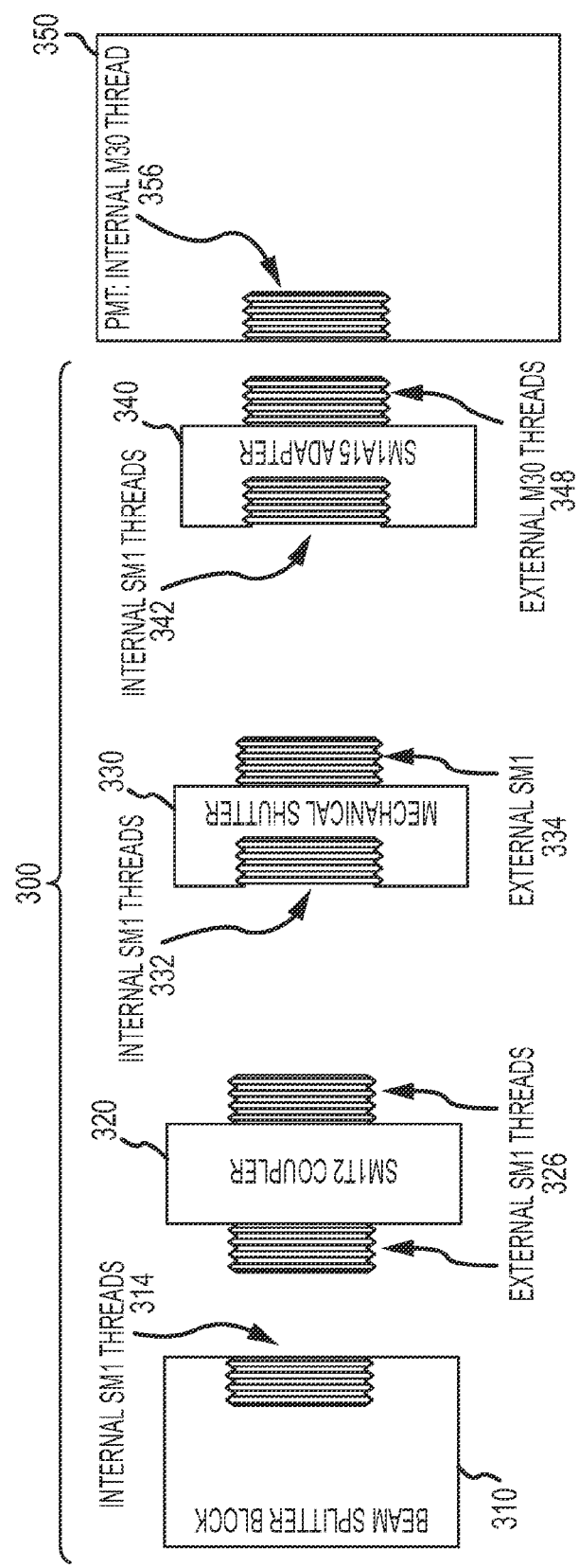
FIG. 3 illustrates an opto-mechanical interface for a photomultiplier tube.

FIG. 3 illustrates an opto-mechanical interface 300 for a photomultiplier tube 350 with an internal thread connection 356. This figure illustrates one method to couple the beam splitter block with the PMT, as shown in FIG. 2 with beam splitter 220 and PMT 240. As shown, the interface 300 includes an internal threaded connection 314 in the beam splitter block 310, and a coupler 320 with external threaded connections 326 is used to couple the beam splitter block 310 with a mechanical shutter 330. To this end, the shutter 330 includes internal threads 332 on one side and external threads 334 on an opposite or other side. An adapter 340 is included in the interface 300 with an internal threaded connection 342 for receiving the external threads 334 of shutter and further with an external threaded connection 348 for coupling the interface 300 with the PMT 350 via internal thread connection 356.

Figure 4:
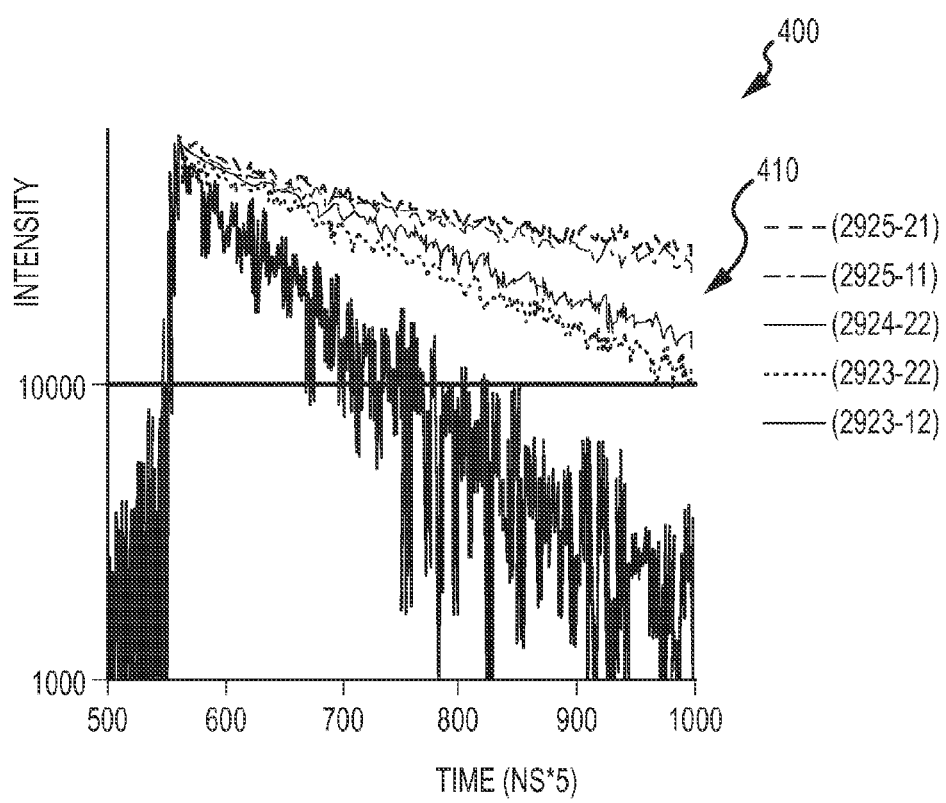
FIG. 4 illustrates photoluminescence decay curves for five CIGS samples.

FIG. 4 illustrates with graph 400 luminescence decay curves 410 for 5 different CIGS samples as measured by a fiber-fed, time-resolved photoluminescence quality control system as disclosed herein (such as system 100 or 200).

Figure 5:
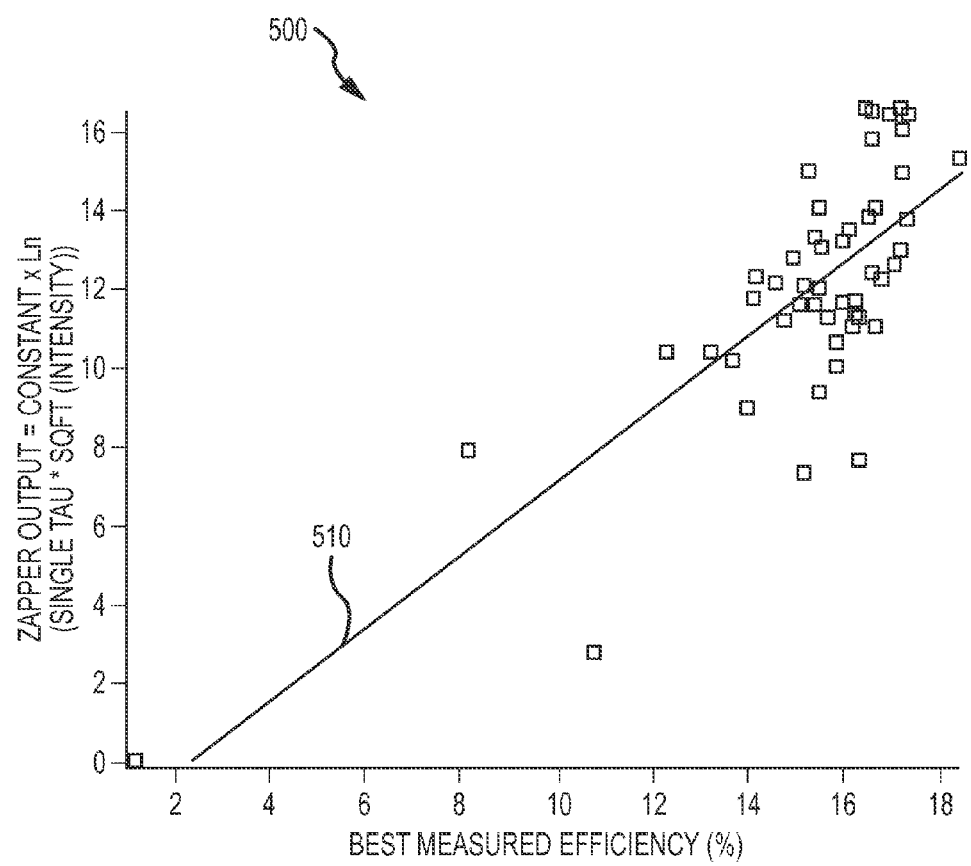
FIG. 5 illustrates a benchtop TRLP system output (y-axis) versus the efficiency of the best device on each piece (x-axis) for 50 different CIGS depositions, where data were acquired without fiber-end optics.

FIG. 5 illustrates a graph 500 presenting Figure of Merit versus the efficiency of the best device on each piece (x-axis) for 50 different CIGS depositions. The desired correlation between final device efficiency and Figure of Merit measured by a benchtop TRPL system (e.g., system 100 or 200) on a bare CIGS film sample (e.g., sample 190 or 290 with a thin film of CIGS providing an absorber for a PV device) is evident from graph 500. This correlation is shown in FIG. 5, where the straight line 510 is a linear fit to the data and the various squares show approximately 50 different CIGS depositions. Scatter in the relationship (i.e., the width of the cloud of squares around the straight line) is approximately ±1.5%. Hence, the quality control system (e.g., system 100 or 200) may be useful for quick feedback on gross process changes. For use as an industrial in-situ sensor that may monitor a nominally constant process, a scatter of ±0.5% may be desirable and readily achieved with the teaching provided herein. The data of FIG. 5 were taken with the sample in close proximity to the fiber carrying the excitation beam, without fiber-end optics, as in FIG. 1. The fiber tip was placed nearly flush with the sample.

Through operation of a prototype of system 200, a large amount of data has been collected that tends to verify the quality control functions described herein or, more simply, that the system 200 works well to provide real time information on the quality of a thin film absorber layer. The prototype of system 200 was used to evaluate a relatively large number of co-evaporated CIGS and CZTS films that were output from three different deposition systems. The films tested were not selected so as to be similar in any manner. They included thin films or absorbers with variations in substrate type, deposition rate, Ga content, sodium incorporation method, and reaction path.

Figure 6:
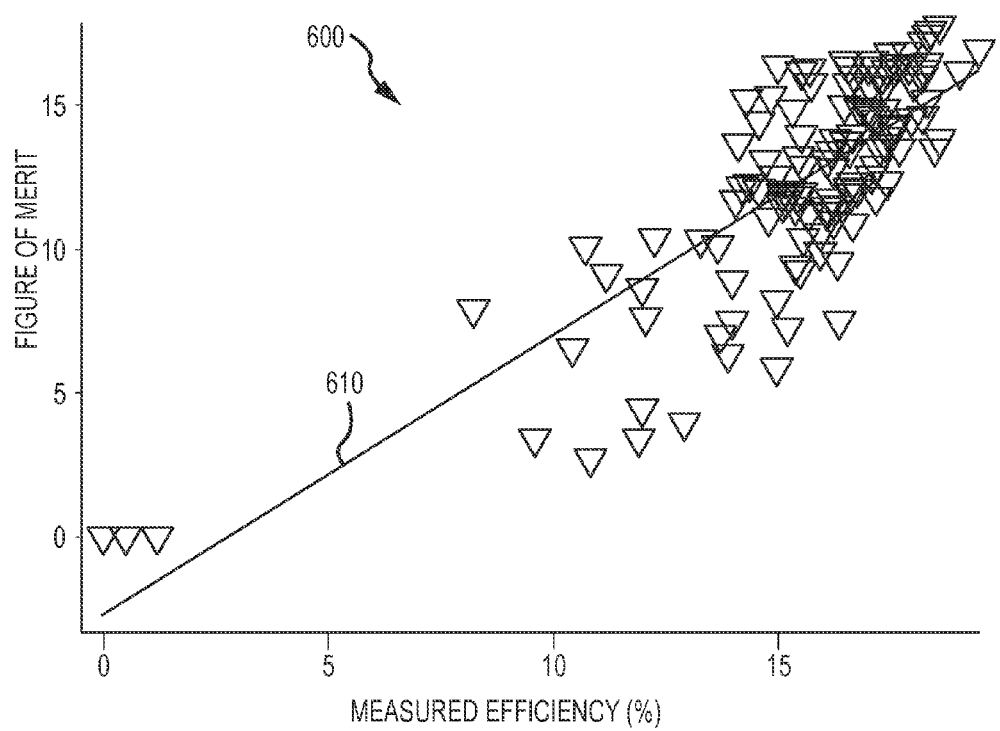
FIG. 6 is a graph presenting results of testing of a quality control system performing analysis of CIGS films showing calculated figure of merit versus measured efficiency, where data were acquired with fiber-end optics utilizing a 600 nm laser.

The effectiveness of the system 200 prototype was evaluated by comparing the output of the prototype, measured on the bare absorber (CIGS or CZTS), against the PV device efficiency obtained later, after completing the device stack with CdS, i-ZnO, ZnO:Al, Ni/Al grids and isolation. An example of such a comparison is shown in FIG. 6 with graph 600. Each data point in FIG. 6 represents one CIGS film. The highest device performance resulting from that CIGS film is shown on the x-axis. On the y-axis is the figure of merit output by the system 200 prototype.

The figure of merit is, thus, a predictor of performance measuring on bare CIGS prior to device formation. The figure of merit is based on both the intensity and time decay (i.e., lifetime) of luminescence measured by the system 200 prototype. The figure of merit has the format: Figure of Merit=constant*ln (decay time*sqrt (intensity)).

The quantities are combined in this fashion since initial luminescence intensity should be proportional to majority carrier density, decay time is the minority carrier lifetime, and lifetime and carrier density combine in the form shown that relates the solar cell voltage to absorber material properties. There is a correlation between the output of the prototype system 200 (e.g. its photodetector, scope, and processing software/hardware) and the final measured efficiency of a PV device, as illustrated by the linear fit to the data shown with line 610. This correlation demonstrates that the system 200 works for its intended purposes discussed herein. There is about ±1.5% scatter in the correlation (evident in the width of the cloud of points around the line 610), but use of a system 100 or 200 in an industrial environment where process set points are not intentionally varied is likely to result in less scatter between the instrument output and the final device efficiency.

The data provided in the graph 600 of FIG. 6 were captured using a 600 nm laser, with appropriately chosen wavelength ranges for the beam splitter and long pass filter. These films are CIGS made in two different deposition chambers. A fiber-end lens assembly was used for these measurements, so that the fiber tip was about a centimeter from the sample.

Figure 7:
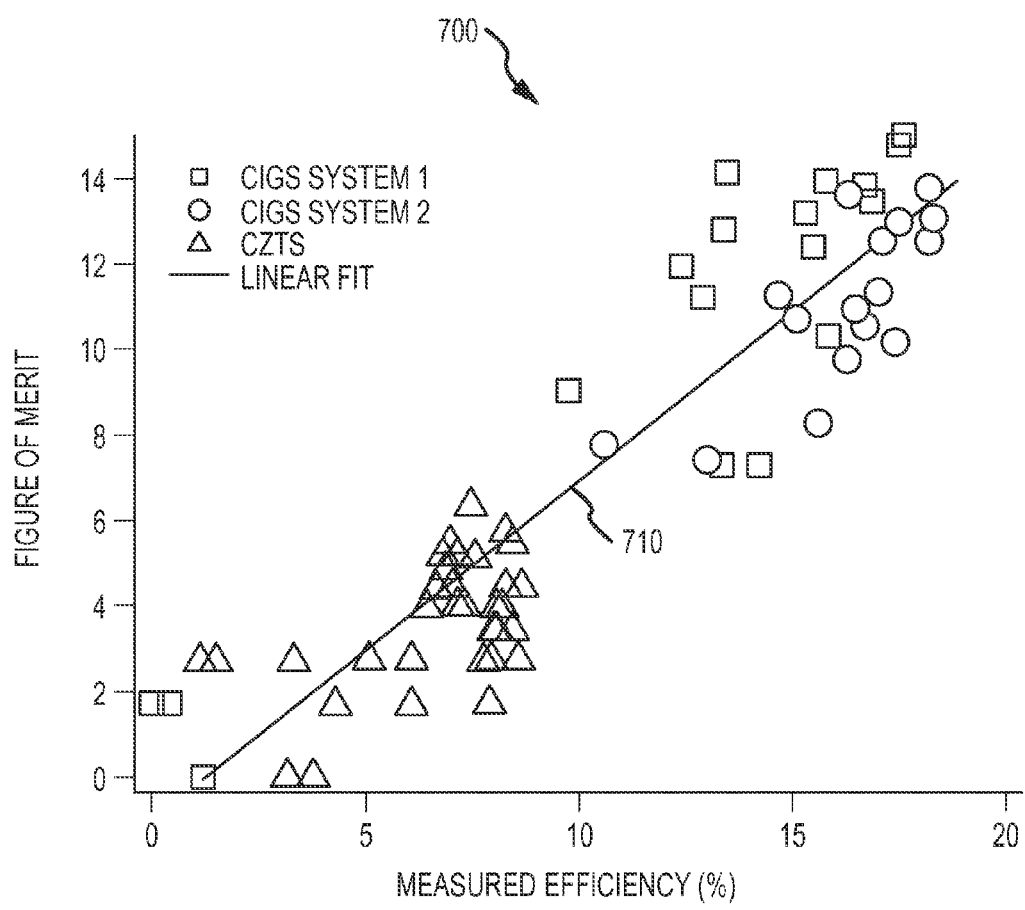
FIG. 7 is a graph similar to that of FIG. 6 showing testing of prototypes with differing films, fiber-end optics, and a 900 nm laser.

Similar experiments were repeated with the results shown in FIG. 7 with graph 700 with linear fit line 710. In this experiment, the prototype of system 200 was outfitted first with a 600 nm laser (CIGS system 1 in graph 700) and then with a 900 nm laser and appropriately chosen beam splitter and long pass filter. This time, a fiber-end lens assembly was used, so that the fiber tip was about a centimeter from the sample. Also, CZTS films and devices were included in the study as shown in graph 700.

A comparison of FIGS. 6 and 7 shows that that the described quality control systems: (a) work for a wide variety of films, and not necessarily just CIGS films; (b) can be used successfully with or without the fiber-end lens assembly (with the best configuration likely being determined by the user's sample and chamber geometry); and (c) can be used with any laser having a photon energy large enough to excite electron-hole pairs in the absorber but small enough to be separated from the PL light by the appropriate beam splitter and long pass filter. With regard to this latter point, for example, a laser providing an exciting beam of less than about 800 nm may be used for a film of CdTe while an exciting beam with less photon energy such as a beam of 630 to 900 nm may be used for a film of CIGS or CZTS. Again, the choice of the particular laser (or its operational settings) typically will be material dependent and may vary to practice the quality control systems discussed herein.

Several means are available to implement the systems and methods discussed in this specification. These means include, but are not limited to, digital computer systems, microprocessors, application-specific integrated circuits (ASIC), general purpose computers, programmable controllers and field programmable gate arrays (FPGAs), all of which may be generically referred to herein as "processors." For example, in one embodiment, signal processing may be incorporated by an FPGA or an ASIC, or alternatively by an embedded or discrete processor. Therefore other embodiments of the present invention are program instructions resident on computer readable media which when implemented by such means enable them to implement various embodiments. Computer readable media include any form of a non-transient physical computer memory device. Examples of such a physical computer memory device include, but are not limited to, punch cards, magnetic disks or tapes, optical data storage systems, flash read only memory (ROM), non-volatile ROM, programmable ROM (PROM), erasable-programmable ROM (E-PROM), random access memory (RAM), or any other form of permanent, semi-permanent, or temporary memory storage system or device. Program instructions include, but are not limited to computer-executable instructions executed by computer system processors and hardware description languages such as Very High Speed Integrated Circuit (VHSIC) Hardware Description Language (VHDL).

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include modifications, permutations, additions, and sub-combinations to the exemplary aspects and embodiments discussed above as are within their true spirit and scope.

The invention claimed is:

1. A system for in-situ photoluminescence, comprising:
a low-power, pulsed diode laser;
a single optical fiber for both transmitting light from the laser to a sample and also for simultaneously collecting and transmitting a photoluminescence (PL) response signal from the sample, wherein the collecting from the sample is for about 10 nanoseconds after the transmitting of the light from the laser;
a filter for receiving the collected PL signal from the optical fiber and removing scattered light;
a broad band detector for detecting a time-resolved photoluminescence of the filtered PL signal for band widths ranging from about 800 nm to about 1300 nm and, in response, forming a signal representative of the time-resolved photoluminescence;
a digitizing component for receiving the time-resolved photoluminescence signal and measuring up to 1 million measurements or more per second of the time-resolved photoluminescence signal; and
a signal processor processing an output of the digitizing component to determine a lifetime correlation of the sample.

2. The system according to claim 1, further comprising a dichroic beam splitter between the laser and the sample, the dichroic beam splitter directing the collected PL signal toward the detector and reducing intensity of the scattered light.

3. The system according to claim 1, wherein the sample comprises a time-resolved CIGS sample.

4. The system according to claim 1, further comprising a fiber-end collimator and focusing lens between the optical fiber and the sample.

5. The system of claim 1, wherein the detecting of the time-resolved photoluminescence comprises measuring decay in photoluminescence with respect to time and wherein the lifetime correlation of the sample comprises a measure of minority carrier lifetime of the sample.

6. The system of claim 1, wherein the lifetime correlation is proportional to the natural logarithm of the product of a measured minority carrier lifetime and the square root of an intensity.

7. A photoluminescence-based system for providing quality control during manufacture of thin film absorber layers for photovoltaic devices, comprising:
a light source comprising a low power, pulsed diode laser for generating an excitation beam;
a single optical fiber with an end both directing the excitation beam onto a thin film absorber layer and simultaneously collecting a time-resolved photoluminescence (TRPL) signal from the thin film absorber layer, wherein a characteristic time period between excitation and photoluminescence is about 10 nanoseconds; and
a processor determining a quality control parameter of the thin film absorber layer based on the collected TRPL signal.

8. The system of claim 7, wherein the processor generates a feedback signal controlling fabrication equipment operable to manufacture a PV device including the thin film absorber layer.

9. The system of claim 7, wherein the laser has a photon energy at least great enough to excite electron hole pairs in the thin film absorber layer.

10. The system of claim 9, wherein the exciting beam generated by the laser is filterable from the collected fluoresced light and wherein the system further includes a filter filtering the collected TRPL signal to remove scattered light.

11. The system of claim 7, wherein the thin film absorber layer comprises a thin film of CIGS, CdTe, or CZTS.

12. The system of claim 7, further comprising a photodetector adapted for detecting a broad photoluminescence spectrum ranging from about 800 nm to about 1300 nm in band widths and for receiving the collected TRPL signal and, in response, generating a detector signal.

13. The system of claim 12, further comprising a digital oscilloscope processing the detector signal and providing the processed detector signal to the processor to determine the quality control parameter.

14. The system of claim 12, wherein the photodetector is a photodiode or a photomultiplier.

15. system of claim 7, wherein the end of the optical fiber is separated from the thin film absorber layer by less than about 1 cm.

16. A system for in-situ time-resolved photoluminescence, comprising:
- a low energy pulsed laser;
- a single optical fiber coupled to the pulsed laser and arranged for transmitting light from the pulsed laser to a thin film sample, the optical fiber also arranged to simultaneously collect a time-resolved photoluminescence (TRPL) signal measuring decay in photoluminescence with respect to time from the thin film sample layer, wherein a characteristic time period between excitation and photoluminescence is about 10 nanoseconds;
- a broad band detector coupled to the optical fiber and arranged to receive the TRPL signal from the optical fiber; and
- a signal processor coupled to the detector, wherein the signal processor determines a quality control parameter for the thin film sample based on the detected TRPL signal.

17. The system of claim 16, wherein the quality control parameter for the thin film sample comprises a minority carrier lifetime of the sample.

18. The system of claim 16, further comprising a digital oscilloscope, wherein the quality control parameter is determined by processing an output signal from the digital oscilloscope.

19. The system of claim 16, wherein the detector arranged to receive the TRPL signal comprises a photomultiplier.

20. The system claim 16, further comprising a filter positioned before the detector to remove scattered light.

21. The system of claim 16, wherein the thin-film sample comprises a CIGS, CZTS, or CdTe sample.

22. The system of claim 16 further comprising a deposition chamber, wherein the thin-film sample is positioned within the deposition chamber.

23. The system of claim 16, wherein the an optical fiber is positioned on a manufacturing line to transmit light from the pulsed laser to the thin film sample when the thin-film sample is positioned on the manufacturing line downstream of a deposition chamber in which the thin film sample is formed.

* * * * *